United States Patent
Wolff et al.

(10) Patent No.: US 10,130,589 B2
(45) Date of Patent: *Nov. 20, 2018

(54) POLYVINYLPYRROLIDONE FOR THE STABILIZATION OF A SOLID DISPERSION OF THE NON-CRYSTALLINE FORM OF ROTIGOTINE

(71) Applicant: UCB Pharma GmbH, Monheim (DE)

(72) Inventors: Hans-Michael Wolff, Monheim (DE); Christoph Arth, Monheim (DE); Luc Quere, Braine-l'Alleud (BE); Walter Müller, Andernach (DE)

(73) Assignees: UCB Pharma GmbH, Monheim (DE); LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,587

(22) Filed: Jan. 31, 2018

(65) Prior Publication Data

US 2018/0147154 A1 May 31, 2018

Related U.S. Application Data

(63) Continuation of application No. 13/515,067, filed as application No. PCT/EP2010/070563 on Dec. 22, 2010, now Pat. No. 9,925,150.

(60) Provisional application No. 61/289,302, filed on Dec. 22, 2009.

(51) Int. Cl.
*A61K 31/381* (2006.01)
*A61K 9/70* (2006.01)

(52) U.S. Cl.
CPC .......... *A61K 9/7069* (2013.01); *A61K 9/7053* (2013.01); *A61K 31/381* (2013.01)

(58) Field of Classification Search
CPC ... A61K 9/7069; A61K 9/7053; A61K 31/381
See application file for complete search history.

(56) References Cited

U.S. PATENT DOCUMENTS

| | | | |
|---|---|---|---|
| 5,177,112 A | 1/1993 | Horn | |
| 5,382,596 A | 1/1995 | Sleevi et al. | |
| 5,676,968 A | 10/1997 | Lipp et al. | |
| 6,372,920 B1 | 4/2002 | Minaskanian et al. | |
| 6,884,434 B1 | 4/2005 | Muller et al. | |
| 7,309,497 B2 | 12/2007 | Rimpler et al. | |
| 7,413,747 B2 | 8/2008 | Mueller et al. | |
| 8,617,591 B2 | 12/2013 | Schacht et al. | |
| 8,754,120 B2 | 6/2014 | Bouwstra et al. | |
| 9,034,914 B2 | 5/2015 | Bouwstra et al. | |
| 9,108,900 B2 | 8/2015 | Scheller et al. | |
| 9,925,150 B2 | 3/2018 | Wolff et al. | |
| 2003/0026830 A1 | 2/2003 | Lauterback et al. | |
| 2003/0027793 A1 | 2/2003 | Lauterback et al. | |
| 2003/0166709 A1 | 9/2003 | Rimpler et al. | |
| 2004/0034083 A1 | 2/2004 | Stephenson et al. | |
| 2004/0048779 A1 | 3/2004 | Schollmayer | |
| 2004/0081683 A1 | 4/2004 | Schacht et al. | |
| 2004/0116537 A1 | 6/2004 | Li et al. | |
| 2004/0137045 A1 | 7/2004 | Breitenbach et al. | |
| 2004/0209861 A1 | 10/2004 | Benavides et al. | |
| 2005/0033065 A1 | 2/2005 | Mueller et al. | |
| 2005/0079206 A1 | 4/2005 | Schacht et al. | |
| 2005/0175678 A1 | 8/2005 | Breitenbach | |
| 2005/0197385 A1 | 9/2005 | Scheller et al. | |
| 2005/0260254 A1 | 11/2005 | Breitenbach et al. | |
| 2006/0216336 A1 | 9/2006 | Wolff | |
| 2006/0263419 A1 | 11/2006 | Wolff | |
| 2007/0072917 A1 | 3/2007 | Scheller et al. | |
| 2007/0093546 A1 | 4/2007 | Scheller et al. | |
| 2007/0191308 A1 | 8/2007 | Kramer | |
| 2007/0191470 A1 | 8/2007 | Scheller | |
| 2007/0197480 A1 | 8/2007 | Scheller et al. | |
| 2008/0008748 A1 | 1/2008 | Beyreuther et al. | |
| 2008/0138389 A1 | 6/2008 | Muller et al. | |
| 2008/0146622 A1 | 6/2008 | Scheller | |
| 2008/0226698 A1 | 9/2008 | Tang et al. | |
| 2008/0274061 A1 | 11/2008 | Schollmayer et al. | |
| 2009/0143460 A1 | 6/2009 | Wolff et al. | |
| 2009/0202647 A1 | 8/2009 | Khunt et al. | |
| 2009/0299304 A1* | 12/2009 | Tang ................... | A61K 9/7061 604/307 |
| 2010/0311806 A1 | 12/2010 | Wolff et al. | |
| 2011/0104281 A1 | 5/2011 | Beyreuther et al. | |
| 2011/0165247 A1 | 7/2011 | Breitenbach | |
| 2013/0251791 A1 | 9/2013 | Seth et al. | |
| 2017/0151215 A1 | 6/2017 | Schollmayer et al. | |

FOREIGN PATENT DOCUMENTS

| | | | | |
|---|---|---|---|---|
| EP | 1 386 605 A1 * | 4/2004 | ............ | A61K 31/38 |
| EP | 1 669 063 A1 | 6/2006 | | |
| EP | 2177217 A1 | 4/2010 | | |
| WO | WO-9407468 | 4/1994 | | |
| WO | 1995/018603 A1 | 7/1995 | | |
| WO | WO-99/49852 A1 | 10/1999 | | |
| WO | WO-02/15903 A2 | 2/2002 | | |

(Continued)

OTHER PUBLICATIONS

International Search Report for WO2011/076879 dated Mar. 14, 2011.

(Continued)

*Primary Examiner* — Yong S. Chong
(74) *Attorney, Agent, or Firm* — Harness, Dickey and Pierce, P.L.C.

(57) ABSTRACT

The present invention relates to a method for stabilizing rotigotine, the method comprising providing a solid dispersion comprising polyvinylpyrrolidone and a non-crystalline form of rotigotine, wherein the weight ratio of rotigotine to polyvinylpyrrolidone is in a range from about 9:3.5 to about 9:6. The present invention also relates to a solid dispersion comprising a dispersing agent and a dispersed phase, said dispersed phase comprising rotigotine and polyvinylpyrrolidone, wherein the weight ratio of rotigotine to polyvinylpyrrolidone is in a range from about 9:3.5 to about 9:6, a pharmaceutical composition comprising such a solid dispersion, in particular a transdermal therapeutic system, as well as a method for the preparation thereof.

24 Claims, 4 Drawing Sheets

(56) References Cited

FOREIGN PATENT DOCUMENTS

| WO | WO-02/089777 A1 | 11/2002 |
|---|---|---|
| WO | WO-03/092677 A1 | 11/2003 |
| WO | WO-2004/012730 A1 | 2/2004 |
| WO | WO-2004/050083 A1 | 6/2004 |
| WO | WO-2005/009424 A1 | 2/2005 |
| WO | WO-2005/063236 A1 | 7/2005 |
| WO | WO-2005/063237 A1 | 7/2005 |
| WO | WO-2005/092331 A1 | 10/2005 |
| WO | WO-2009/068520 A2 | 6/2009 |

OTHER PUBLICATIONS

Office Action dated Oct. 10, 2013 issued in U.S. Appl. No. 13/515,067.
Office Action dated Nov. 14, 2013 issued in U.S. Appl. No. 13/515,067.
Office Action dated Apr. 17, 2014 issued in U.S. Appl. No. 13/515,067.
Office Action dated Mar. 22, 2016 issued in U.S. Appl. No. 13/515,067.
Office Action dated Jun. 23, 2017 issued in U.S. Appl. No. 13/515,067.
Office Action dated May 30, 2013 issued in U.S. Appl. No. 13/515,067.
Office Action, dated Aug. 15, 2012 issued in U.S. Appl. No. 13/020,414.
Office Action, dated Aug. 3, 2010 issued in U.S. Appl. No. 10/517,157.
Office Action, dated Jan. 24, 2012 issued in U.S. Appl. No. 13/020,414.
Office Action, dated Nov. 24, 2009 issued in U.S. Appl. No. 10/517,157.
Van der Weide, et al. (1988) "The enantiomers of the D-2 dopamine receptor agonist N-0437 discriminate between pre- and postsynaptic dopamine receptors." Eur J Pharmacol 146:319-326.
Office Action dated Jul. 26, 2018 issued in U.S. Appl. No. 15/892,744.
Chaudhuri, R. (2008), "Crystallisation within transdermal rotigotine patch: is there cause for concern?", *Expert Opin. Drug Deliv.*, 5(11): 1169-1171.
UCB Inc., Request to initiate Neupro® down-titration, Healthcare Provider Letter, Mar. 21, 2008.
Waknine, Y., "Rotigotine Patch Recalled Due to Drug Crystallization", *Medscape*—Apr. 9, 2008.
UBM Media, LLC, Apr. 14, 2008, "Neupro patches recalled due to crystallization", *Drug Topics*.
UCB News, Jun. 20, 2007, Press Release—Regulated information, "UCB advises US-physicians to down-titrate patients on Neupro® in view of out-of-stock situation in US".
Office Action dated Apr. 7, 2009 issued in U.S. Appl. No. 10/565,713.
Office Action dated Dec. 7, 2009 issued in U.S. Appl. No. 10/565,713.
Office Action dated Oct. 23, 2009 issued in U.S. Appl. No. 10/565,699.
Office Actoin dated May 27, 2010 issued in U.S. Appl. No. 10/565,699.
Office Action dated Feb. 14, 2011 issued in U.S. Appl. No. 10/565,699.
Office Action dated Nov. 8, 2011 issued in U.S. Appl. No. 10/565,699.
Office Action dated Jun. 11, 2012 issued in U.S. Appl. No. 12/744,989.
Office Action dated Apr. 24, 2013 issued in U.S. Appl. No. 10/565,699.
Office Action dated Aug. 28, 2018 issued in U.S. Appl. No. 15/982,744.
U.S. Appl. No. 15/982,744, filed May 17, 2018.
Zydus Worldwide DMCC and Zydus Pharmaceuticals (USA) Inc.'s Answer, Affirmative Defenses, and Counterclaims to Plaintiffs' Amended and Supplemental Complaint for Patent Infringement.
Zydus Worldwide DMCC and Zydus Pharmaceuticals (USA) Inc.'s Initial Invalidity Contentions for U.S. Pat. No. 9,925,150.

\* cited by examiner

POLYVINYLPYRROLIDONE FOR THE STABILIZATION OF A SOLID DISPERSION OF THE NON-CRYSTALLINE FORM OF ROTIGOTINE

CROSS-REFERENCE TO RELATED APPLICATIONS

This patent application is a continuation of U.S. Ser. No. 13/515,067 filed 11 Jun. 2012, which is a National Phase entry of International Application No. PCT/EP2010/070563 filed on 22 Dec. 2010, which claims the benefit of U.S. Application No. 61/289,302 filed on 22 Dec. 2009. The entire disclosures of each of the above recited applications are incorporated herein by reference.

FIELD

The present invention relates to the use of polyvinylpyrrolidone for the stabilization of a solid dispersion of the non-crystalline form of rotigotine, the use of such a stabilized solid dispersion for the preparation of a transdermal therapeutic system and a transdermal therapeutic system comprising such a stabilized solid dispersion as a self adhesive matrix, which is characterized by an increased long term storage stability due to the reduced formation of rotigotine crystals.

BACKGROUND

Rotigotine is the International Non-Proprietary Name (INN) of the compound (−)-5,6,7,8-tetrahydro-6-[propyl-[2-(2-thienyl)ethyl]-amino]-1-naphthalenol having the structure shown below

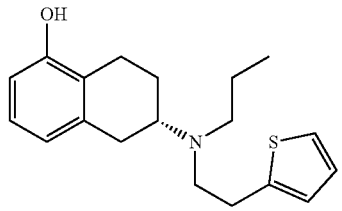 [SMILES: CCCN(CCc1cccs1)[C@H]1CCc2c(O)cccc2C1]

Two crystalline forms of rotigotine are presently known: polymorphic form I and polymorphic form II (WO 2009/068520). They can be differentiated by their respective physicochemical parameters, i.e. differing powder X-ray diffraction spectra, Raman spectra and melting points. At room temperature, the crystalline polymorphic form II is more stable than form I, which in turn is more stable than the amorphous form of rotigotine.

Rotigotine is a non-ergolinic D1/D2/D3 dopamine agonist that resembles dopamine structurally and has a similar receptor profile but a higher receptor affinity.

In contrast to other non-ergolinic dopamine agonists, rotigotine has significant D1 activity, which may contribute to a more physiological action.

In contrast to ergolinic compounds, rotigotine has a very low affinity for 5 $HT_{2B}$ receptors and thus a low risk of inducing fibrosis.

Actions on non-dopaminergic receptors (such as 5-$HT_{1A}$ agonism and $A_{2B}$ antagonism) may contribute to other beneficial effects, such as antidyskinetic activity, neuroprotective activity and antidepressive effects.

Rotigotine is disclosed as active agent for treating patients suffering from Parkinson's disease (described in WO 2002/089777), Parkinson's plus syndrome (described in WO 2005/092331), depression (described in WO 2005/009424) and the restless-legs syndrome (described in WO 2003/092677) as well as for the treatment or prevention of dopaminergic neuron loss (described in WO 2005/063237) and treatment of pain (PCT/EP2007/005381).

Known pharmaceutical compositions containing rotigotine comprise a transdermal therapeutic system or patch (TTS) (described inter alia in WO 99/49852), a depot form (described in WO 02/15903), an iontophoretic device (described in WO 2004/050083) and an intranasal formulation (described in WO 2005/063236).

To date, various TTS for the administration of amine functional drugs, such as rotigotine and many others, have been described.

WO 94/07468 discloses a TTS containing rotigotine hydrochloride as active substance in a two-phase matrix, which is essentially formed by a hydrophobic polymer material as the continuous phase and a disperse hydrophilic phase contained therein and mainly containing the drug and hydrated silica. The silica is said to enhance the maximum possible loading of the TTS with the hydrophilic salt. Moreover, the formulation of WO 94/07468 usually contains additional hydrophobic solvents, permeation promoting substances, dispersing agents and, in particular, an emulsifier, which is required to emulsify the aqueous solution of the active component in the lipophilic polymer phase. A TTS prepared by using such a system has been tested in healthy subjects and Parkinson's patients. However, no satisfactory drug plasma levels were achieved.

Various further TTS have been described in WO 99/49852. Various further transdermal therapeutic systems have been described in WO 99/49852. The TTS used in this patent application comprise a backing layer, inert with respect to the constituents of the matrix, a self-adhesive matrix layer containing an effective quantity of rotigotine or rotigotine hydrochloride and a protective film which is to be removed before use. The matrix system is composed of a non-aqueous polymer adhesive system, based on acrylate or silicone.

Further TTS for the delivery of rotigotine are for example disclosed in EP 1 256 339 and in WO 2004/012730. These systems utilize a mixture of at least one high tack and at least one medium tack amine-compatible silicone pressure sensitive adhesive as the main adhesive components of the self adhesive matrix. They provide for better flux rates and sufficient rotigotine plasma levels.

Despite the existence of TTS comprising rotigotine in the prior art, there remains room for improvement in such TTS, and in processes for making them.

Crucial pharmaceutical aspects of the TTS are the drug release profile, distribution of the drug within the patch, drug solubility in the matrix, drug and/or patch stability, adhesiveness of the patch to the skin, smooth and complete removability of the patch from the skin.

As these parameters are influencing each other it is difficult to develop a new patch just by amending one parameter.

Recently, it has been found that the systems as described above unfortunately show long-term stability problems. If rotigotine crystals are formed in the self adhesive matrix during long term storage, crystal growth can lead to reduced release rates of rotigotine with the risk eventually falling below the specified values.

Due to the occurrence of a new polymorphic form (form II) of the drug substance rotigotine crystal formation on the commercialized patches can take place. An attempt to modify the manufacturing process resulted only in very limited success. These patches still require cold storage until administration to the skin. This results inter alia in a more complicated application instructions for the rotigotine patch, like that the cooled drug product should be taken out of the refrigerator at least 1 hour before application and the adhesive on the patch has to be warmed up when the patch is applied In general, it is well known in the art that stabilizing the amorphous state of a drug substance in a pharmaceutical dosage form including transdermal systems can be very difficult, if as in the case of rotigotine, the amorphous form is only metastable and easily converts into crystals. In such a case, the self adhesive matrix as a whole represents a metastable solid dispersion.

It is, therefore, an object of the present invention to provide a TTS comprising rotigotine which does not exhibit the above described drawbacks. In particular, the TTS should display an appropriate drug release profile combined with adequate stability and should be stable at room temperature.

SUMMARY OF THE INVENTION

It is now surprisingly found that when used in a specific weight ratio to rotigotine, PVP is unexpectedly able to stabilize the non-crystalline form of rotigotine and prevent rotigotine from re-crystallization in a solid dispersion, such as a self adhesive matrix of a transdermal therapeutic system, thereby imparting sufficient long term storage stability properties to the transdermal therapeutic system, preferably at room temperature, and without negatively influencing other relevant parameters of the TTS.

Room temperature or ambient as used in the present application is to be understood to apply to a range from 15° C. to 25° C. In one embodiment the room temperature is in a range from 18° C. to 22° C. and in another embodiment it is about 20° C.

In a first aspect, the present invention relates to the use of polyvinylpyrrolidone for the stabilization of a solid dispersion of the non-crystalline form of rotigotine in a dispersing agent, wherein the weight ratio of rotigotine to polyvinylpyrrolidone ranges from about 9:3.5 to about 9:6.

In one embodiment, the weight ratio of rotigotine to polyvinylpyrrolidone ranges from about 9:3.5 to about 9:4.5.

In a further embodiment, the solubility of rotigotine in the dispersing agent without a stabilizer (e.g. PVP) is below 5 wt-%.

In one embodiment, the dispersing agent comprises at least one adhesive having a complex viscosity between 40 and 250 MP.

In a further embodiment, the dispersing agent additionally comprises at least one second adhesive having a complex viscosity between 1 and 10 MP.

In one embodiment the complex viscosity of the dispersing agent comprising a mixture of adhesives is between 5 and 25 MP, preferably between 6 and 20 MP.

In one further embodiment, the complex viscosity of the solid dispersion comprising a mixture of adhesives as dispersing agent and rotigotine and polyvinylpyrrolidone in the dispersed phase is between 5 and 15 MP, preferably between 6 and 15 MP.

In a further aspect, the present invention relates to a solid dispersion comprising a mixture of adhesives as dispersing agent and rotigotine and polyvinylpyrrolidone in the dispersed phase, wherein the solid dispersion has a peel adhesion between 3 and 16 N/50 mm at a thickness of 50 g/m² and/or a peel adhesion between 14 and 26 N/50 mm at a thickness of 150 g/m².

In still a further aspect, the present invention relates to a solid dispersion comprising a mixture of adhesives as dispersing agent and rotigotine and polyvinylpyrrolidone in the dispersed phase, wherein the solid dispersion has a static shear adhesion between 20 and 150 min.

In another embodiment, the dispersing agent comprises at least one silicone pressure sensitive adhesive and preferably a mixture of at least one high tack and at least one medium tack silicone pressure sensitive adhesive.

In still another embodiment, the solid dispersion contains rotigotine and the polyvinylpyrrolidone in a multitude of microreservoirs.

In one embodiment of the invention, the solid dispersion is a self adhesive matrix of a transdermal therapeutic system.

In a further aspect, the present invention relates to a solid dispersion comprising a dispersing agent and a dispersed phase, said dispersed phase comprising rotigotine and polyvinylpyrrolidone, wherein the weight ratio of rotigotine to polyvinylpyrrolidone ranges from about 9:3.5 to about 9:6

In an embodiment the weight ratio of rotigotine to polyvinylpyrrolidone in the solid dispersion ranges from about 9:3.5 to about 9:4.5.

In a further embodiment the solubility of rotigotine in the dispersing agent of the solid dispersion without a stabilizer (e.g. PVP) is below about 0.1 wt-%.

In another embodiment, the dispersing agent of the solid dispersion comprises at least one silicone pressure sensitive adhesive. More preferably, it comprises a mixture of at least one high tack and at least one medium tack silicone pressure sensitive adhesive.

In still another embodiment, the solid dispersion comprises rotigotine and polyvinylpyrrolidone in a multitude of microreservoirs.

In another aspect, the present invention relates to the use of the above specified solid dispersion for the preparation of a transdermal therapeutic system, which comprises the solid dispersion as self adhesive matrix.

In another aspect, the present invention relates to a transdermal therapeutic system comprising the above specified solid dispersion.

In still another aspect, the present invention relates to the use of the aforementioned transdermal therapeutic systems as medicaments.

DETAILED DESCRIPTION

Figure 1:
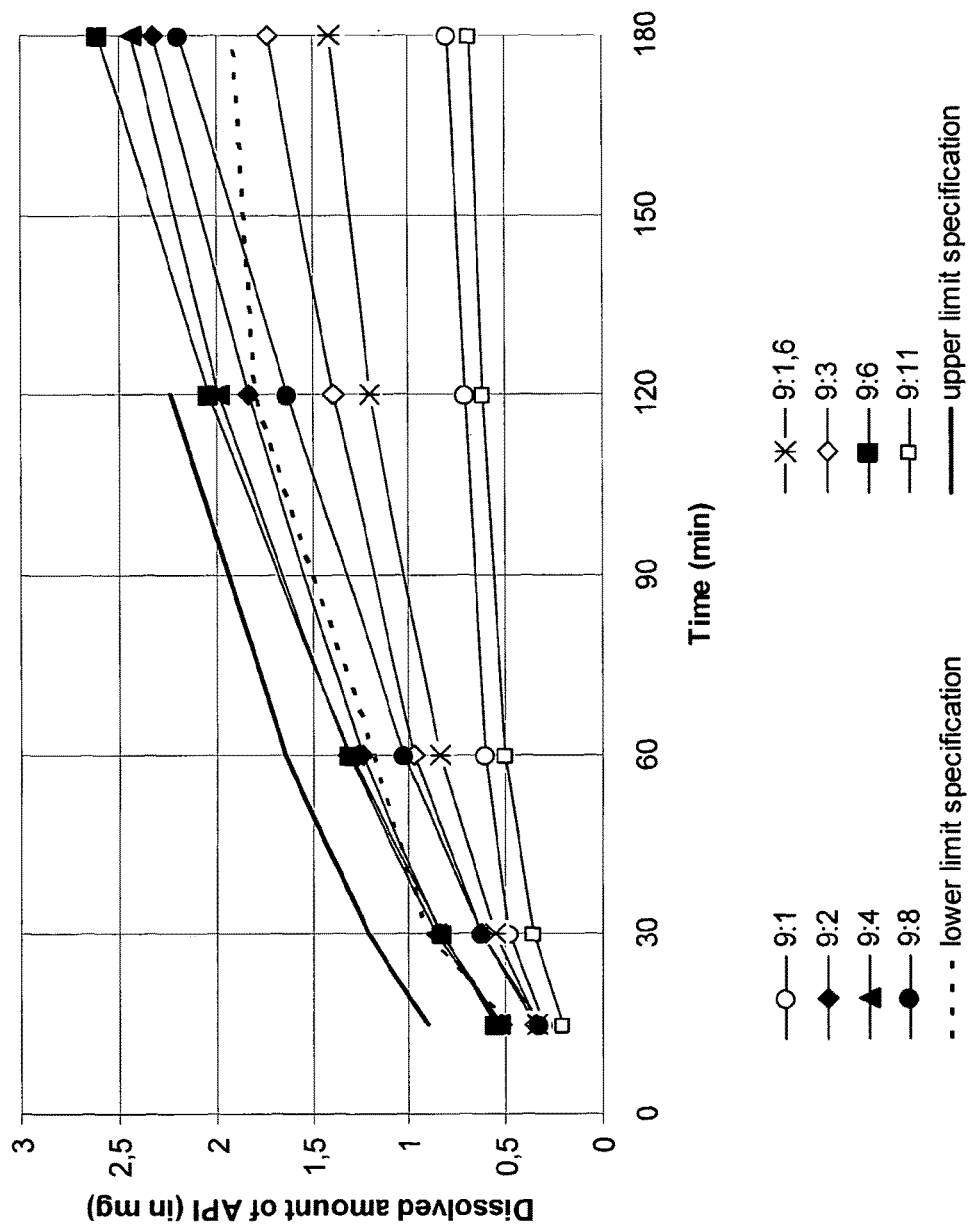
FIG. 1 shows the influence of varying rotigotine to polyvinylpyrrolidone weight ratios on the release of rotigotine from a TTS. API=active pharmaceutical ingredient (rotigotine); PVP=polyvinylpyrrolidone. "Specification" is related to the product specification of the existing Neupro® Rotigotine patch.

Polyvinylpyrrolidone (PVP) is a polymer made from the monomer N-vinylpyrrolidone. It increases the cohesion of silicone adhesives. The molecular weight of the polyvinylpyrrolidone can be in the range from 2,000 to 2,500,000 Dalton (g/mol) (given as weight average), in one embodiment in the range from 700 000 to 1,500,000, in another embodiment in the range from 1,000,000 to 1,500,000 dalton. Various grades of PVP are commercially available from e.g. BASF Aktiengesellehaft of Ludwigshafen, Germany, e.g. under the name of Kollidon. For example, the following grades of Kollidons are water soluble forms of PVP: K-12 PF (molecular weight=2,000-3,000); K-17 PF (molecular weight=7,000-11,000); K-25 (molecular weight=28,000-34,000); K-30 (molecular weight=44,000-54,000); and K-90F (molecular weight=1,000,000-1,500,000). In a preferred embodiment, the molecular weight of the polyvinylpyrrolidone is in the range from 28,000 to 1,500,000 Dalton (g/mol). Particularly preferred are the Kollidon grades K-25, K-30 and K-90F.

It is known from previous experiments that PVP reduces drug release from transdermal delivery systems with rotigotine across lipophilic membranes. Surprisingly it has been found, that a variation of the rotigotine/PVP weight ratio from a range of about 9:2 to about 9:6, and in one embodiment about 9:4, has only a very small effect on drug skin permeation but a highly significant impact on physical stability of the patch.

The present invention is based on the finding that when rotigotine and polyvinylpyrrolidone are employed in a specific weight ratio, polyvinylpyrrolidone is able to stabilize solid dispersions of the non-crystalline form of rotigotine by preventing rotigotine from crystallization.

Thus, the present invention relates in one aspect to the use of polyvinylpyrrolidone for the stabilization of a solid dispersion of non-crystalline form of rotigotine in a dispersing agent.

According to the present invention, polyvinylpyrrolidone was found to stabilize non-crystalline rotigotine in the solid dispersion state when the two components are used in a weight ratio of rotigotine to polyvinylpyrrolidone, which ranges from about 9:3.5 to about 9:6 and in another embodiment from about 9:3.5 to about 9:4.5 and in still another embodiment is 9:4.

In another aspect, the present invention relates to a solid dispersion comprising rotigotine and polyvinylpyrrolidone, wherein the weight ratio of rotigotine to polyvinylpyrrolidone ranges from about 9:3.5 to about 9:6, in another embodiment from 9:3.5 to 9:4.5.

In a further embodiment the solid dispersion comprises rotigotine and polyvinylpyrrolidone in a weight ratio of 9:4.

It will be appreciated by the skilled person that any multiple of the above weight ratios will also be encompassed by the present invention. That is, the weight ratio of rotigotine to polyvinylpyrrolidone of 9:4 for example also encompasses the weight ratio of 18:8 and the weight ratio of rotigotine to polyvinylpyrrolidone of 9:3.5 for example also encompasses the weight ratio of 13.5:5.25.

The term "stabilization" as used herein means that the non-crystalline form of rotigotine in a solid dispersion is maintained due to preventing rotigotine from crystallization over a certain period of time under defined conditions. In particular, a stabilization of at least 2 years under storage at room temperature or temperatures not exceeding 25° C. is intended. This means that degree of rotigotine crystallization in the solid dispersion should not exceed 10%, more preferably should not exceed 5% and most preferably should not exceed 2% (all percentages used herein are by weight, unless provided otherwise), based on the initial amount of rotigotine in the solid dispersion after 24 months storage in a sealed container at room temperature.

In one embodiment the non-crystalline form of rotigotine is amorphous rotigotine.

The term "solid dispersion" as used herein refers to a metastable system consisting of a dispersing agent and a dispersed phase, which is immiscible with the dispersing agent.

The dispersing agent of the solid dispersion may be any solid or semi-solid semi-permeable silicone-based polymer or copolymer or in another embodiment the dispersing agent is an acrylate. The dispersing agent should provide sufficient activity and stability for the solid dispersion as well as sufficient release of rotigotine.

Usually this polymer will be a pressure sensitive adhesive (PSA) or a mixture of such adhesives.

In one embodiment, the dispersing agent comprises at least one adhesive having a complex viscosity between 40 and 250 MP (mega-poise, i.e. 1 million poise; 1 P (poise) corresponds to 1 g/(cm*s) or 0.1 kg/(m*s), i.e. 0.1 Pa*s), in another embodiment between 50 and 200 MP and in still another embodiment between 60 and 150 MP and in a further embodiment the complex viscosity is between 70 and 120 MP.

It was surprisingly found that a sufficient physical long-term stability of the solid drug dispersion can be achieved by when the upper complex viscosity is below 250 MP and most preferably below 200 MP.

In a further embodiment, the dispersing agent comprises at least one second adhesive having a complex viscosity between 1 and 10 MP, in another embodiment between 1.5 and 5 MP and in still another embodiment between 2 and 3 MP.

In one embodiment the complex viscosity of the mixture of adhesives is between 5 and 25 MP. In another embodiment the complex viscosity of the mixture of adhesives is between 6 and 20 MP. In another embodiment the complex viscosity of the mixture of adhesives is between 7 and 15 MP and in still another embodiment between 8 and 12 MP.

In one further embodiment, the complex viscosity of the solid dispersion comprising a mixture of adhesives as dispersing agent and rotigotine and polyvinylpyrrolidone in the dispersed phase is between 5 and 15 MP, in another embodiment between 6 and 15 MP, in another embodiment between 8 and 15 MP and in still another embodiment between 10 and 12 MP.

Complex viscosity was determined by using a Stress Tech Rheometer (REOLOGICA Instruments AB or equivalent) being equipped with plate/plate measurement system with d=25 mm and a temperature regulator capable to adjust the temperature between 15 and 110° C. All rheology tests were done in the linear viscoelastic region of the test material at an oscillation frequency of 0.1 rad/s and 30° C. Depending on the complex viscosity of the respective samples, the following parameters were used:

a) adhesives having a complex viscosity between 40 and 250 MP: thickness of the sample films: about 2 mm; strain: 5%; gap: 1.5 mm; and
b) adhesives having a complex viscosity between 1 and 10 MP: thickness of the sample films: about 3 mm; strain: 1%, gap: 2.5 mm.

In a further aspect, the present invention relates to a solid dispersion comprising a mixture of adhesives as dispersing agent and rotigotine and polyvinylpyrrolidone in the dispersed phase, wherein the solid dispersion has a peel adhesion at a thickness of 50 g/m² between 3 and 16 N/50 mm, in another embodiment between 4.5 and 14 N/50 mm and in still another embodiment between 6 and 12 N/50 mm, and/or has a peel adhesion at a thickness of 150 g/m² between 1.4 and 26 N/50 mm, in another embodiment between 16 and 24 N/50 mm, in still another embodiment between 17 and 23 N/50 mm and in a further embodiment around 20.1 N/50 mm.

Peel adhesion was determined by using a tensile test machine (ZWICK/ROELL Z2.5 or equivalent). Samples were mounted on a suitable test plate made of aluminium and left for 10 min before peeling off. The sample films had a thickness of 50 g/m² or of 150 g/m². All measurements were done with a peel speed of 300 mm/min and a peel angle of 90° at room temperature.

In still a further aspect, the present invention relates to a solid dispersion comprising a mixture of adhesives as dispersing agent and rotigotine and polyvinylpyrrolidone in the dispersed phase, wherein the solid dispersion has a static shear adhesion between 20 and 150 min, in another embodiment between 25 and 100 min, in still another embodiment between 30 and 80 min and in a further embodiment the static shear adhesion is between 40 and 60 min.

Static shear adhesion was determined using a method based on DIN standard method EN 1943:2003-01 "Adhesive tapes, measurement of the shear force under static load". In brief, for the determination of the shear force, a defined area (12 mm×12 mm) of a sample film was stuck on a test plate made of V2A steel and is rolled twice with constant pressure (roll: m 5 kg, width=2.5 cm) in longitudinal direction for ca. 1 sec. Afterwards, the test plate was vertically arranged and a standard weight (1000±5 g) was attached at the free end of the sample. The time until failure of the adhesive sealing of the sample, i.e. the time until the weight drops down, was measured. All measurements were done at 23±2° C. and 50±5% RH. Before, the samples were allowed to equilibrate under these standard conditions for at least 24 h.

The adhesives used in the present invention should preferably be pharmaceutically acceptable in a sense that they are biocompatible, non-sensitising and non-irritating to the skin of the recipient. Particularly advantageous adhesives for use in the present invention should further meet the following requirements:

1. retained adhesive and co-adhesive properties in the presence of moisture or perspiration, under normal temperature variations; and
2. good compatibility with rotigotine, as well as with the further excipients.

Although different types of pressure sensitive adhesives may be used in the present invention, it is preferred to use lipophilic adhesives having both low drug and low water absorption capacity. Preferably, the adhesives have solubility parameters which are lower than those of rotigotine. Such preferred pressure sensitive adhesives are amine-compatible silicone type pressure sensitive adhesives.

In a preferred embodiment the dispersing agent comprises at least one silicone pressure sensitive adhesive and preferably a mixture of at least one high tack and at least one medium tack silicone pressure sensitive adhesive.

Especially preferred pressure sensitive adhesives are of the type forming a soluble polycondensed polydimethylsiloxane (PDMS)/resin network, wherein the hydroxy groups are capped with e.g. trimethylsilyl (TMS) groups. Preferred adhesives of this kind are the BIO-PSA silicone pressure sensitive adhesives manufactured by Dow Corning, particularly the Q7-4201 and Q7-4301 qualities.

However, other silicone adhesives may also be used.

Tack has been defined as the property that enables an adhesive to form a bond with the surface of another material upon brief contact under light pressure (see e.g. "Pressure Sensitive Tack of Adhesives Using an inverted Probe Machine", ASTM D2979-71 (1982); H. F. Hammond in D. Satas "Handbook of Pressure Sensitive Adhesive Technology" (1989), 2nd ed., Chapter 4, Van Nostrand Reinhold, New York, page 38).

Medium tack of a silicone pressure sensitive adhesive indicates that the immediate bond to the surface of another material is weaker compared to a high tack silicone adhesive.

The mean resin/polymer ratio is approx. 60/40 for medium tack adhesives, whereas it is approx. 55145 for high tack adhesives. It is known to the skilled person that both tape and rheological properties are significantly influenced by the resin/polymer ratio (K. L. Ulman and R. P. Sweet "The Correlation of Tape Properties and Rheology" (1998), Information Brochure, Dow Corning Corp., USA).

Blends comprising a high tack and a medium tack silicone type pressure sensitive adhesive comprising polysiloxane with a resin are advantageous in that they provide for the optimum balance between good adhesion and little cold flux. Excessive cold flux may be disadvantageous since it results in too soft solid dispersions.

Preferably, the weight ratio of a high tack to a medium tack silicone type pressure sensitive adhesive in these blends is 1:1. However, this does not exclude employing any other weight ratio.

A mixture of the aforementioned. Q7-4201 (medium tack) and Q7-4301 (high tack) qualities proved to be especially useful for the preparation of a solid dispersion according, to the present invention.

The solid or semi-solid semi-permeable polymer forming the dispersing agent has to satisfy the following requirements:

1. Sufficient solubility and permeability for the free base form of rotigotine.
2. Impermeability for the protonated form of rotigotine.

In one embodiment the solubility of rotigotine (without stabilizer) in the dispersing agent is about 5 wt-% or below and in another embodiment about 3 wt-% or below. In still another embodiment the solubility of rotigotine (without stabilizer) in the dispersing agent is about 2 wt-% or below and in another embodiment it is about 0.1 wt-% or below.

The dispersed phase of the solid dispersion comprises rotigotine in non-crystalline form and a stabilizer, for example polyvinylpyrrolidone, and optionally further pharmaceutically acceptable excipients, such as permeation enhancers and antioxidants. In one embodiment the stabilizer is selected from polyvinylpyrrolidone and in a preferred embodiment from water soluble polyvinylpyrrolidone. Copolymers of polyvinylpyrrolidone and vinyl acetate, polyethyleneglycol, polypropyleneglycol, glycerol and fatty acid esters of glycerol or copolymers of ethylene and vinylacetate might also be considered for such use.

Suitable permeation enhancers may be selected from the group of fatty alcohols, fatty acids, fatty acid esters, fatty acid amides, glycerol or its fatty acid esters, N-methylpyrrolidone, terpenes such as limonene, [alpha]-pinene, [alpha]-terpineol, carvone, carveol, limonene oxide, pinene oxide, 1,8-eucalyptol and most preferably ascorbyl palmitate.

Suitable antioxidants are sodium metabisulfite, ascorbylpalmitate and DL-alpha tocopherol.

Unless expressly indicated otherwise, any references to rotigotine in the context of this invention and the claims of this application mean rotigotine in the form of its free base. In some cases, however, traces of rotigotine hydrochloride may be contained in a rotigotine preparation but these traces typically do not exceed 5 wt-%, based on the amount of the free base. More preferably the content of hydrochloride impurities should be less than 2 wt-%, even more preferably less than 1 wt-% and most preferably the rotigotine used in the present invention contains less than 0.1 wt-% or no hydrochloride impurities at all.

A further step, which may be taken for reducing the amount of the salt form of rotigotine, is isolating the free base form of rotigotine in solid form prior to the preparation of the solid dispersion. If the free base of rotigotine is produced in situ during the manufacture of the solid dispersion by neutralizing an acid addition salt, a certain residue of the ionized drug form will remain (usually >5 wt-% and up to approximately 10 w-%). Therefore, such in situ preparation of the free base form will generally not be suitable for practising the present invention.

It will be understood by a person skilled in the art that rotigotine exists in various isomeric forms. It thus has also to be understood that any single isomer or a mixture of different isomers may be used in the present invention. Hence, the S- or R-enantiomer or the racemate or any other enantiomeric mixture of rotigotine may be used.

In one embodiment of the invention the water content of the solid dispersion is less than 0.4 wt-% and in another embodiment it less than 0.2 wt-% related to the total patch matrix.

In one embodiment, high molecular weight polyvinylpyrrolidone (PVP) having a molecular weight of about 1 Mio Da is employed in the present invention. Rotigotine mixtures with these high molecular weight povidone grades result in a high degree of drug immobilization at room temperature. However the glass temperature of mixtures of rotigotine/PVP with a weight ratio in the range of about 9:3.5 to 9:6 is low enough to enable sufficiently high drug release at skin temperature. In one embodiment this range is 9:3.5 to 9:4.5 and in another the weight ratio is about 9:4.

While not wishing to be bound by theory it is believed that free rotigotine is molecularly dispersed in the dispersing agent (outer phase) and that a non crystalline form of rotigotine is reversibly associated with PVP by forming an inner phase or microreservoir. In one embodiment the non-crystalline form of rotigotine is amorphous rotigotine. One advantage of a stable solid drug dispersion is that it can significantly reduce constraints often caused by low drug solubility in polymers suitable for transdermal delivery.

This does not exclude and will normally even imply that a certain fraction of rotigotine is dissolved in the dispersing agent of the solid dispersion at its saturation concentration.

The term "microreservoirs" as used herein is meant to be understood as particulate, spatially and functionally separate compartments consisting of a mixture of rotigotine and polyvinylpyrrolidone, which are dispersed in the dispersing agent of the solid dispersion. In one embodiment the solid dispersion contains $10^3$ to $10^9$ microreservoirs per $cm^2$ of its surface, in another embodiment this in the range of $10^6$ to $10^9$ microreservoirs per $cm^2$.

The maximum diameter of the microreservoirs is less than the thickness of the solid dispersion, preferably up to 85% of the thickness of the solid dispersion, particularly preferably 5 to 74% of the thickness of the solid dispersion. For an exemplary thickness of the solid dispersion of 50 μm this corresponds to a maximum diameter of the microreservoirs in the range of preferably up to approx 40 to 45 μm.

The term "maximum diameter" as used herein is meant to be understood as the diameter of the microreservoirs in one dimension (x-, y-, or z-dimension), which is the largest. It is clear to the skilled person that in case of spherical diameters the maximum diameter corresponds to the microreservoir's diameter. However, in the case of microreservoirs, which are not shaped in the form of spheres, i.e. of different geometric forms-, the x-, y- and z-dimensions may vary greatly.

In a particularly preferred embodiment of the invention, the mean diameter of the rotigotine containing microreservoirs distributed in the solid dispersion is in the range of 1 to 40%, even more preferably 1 to 20%, of the thickness of the solid dispersion. For an exemplary thickness of the solid dispersion of 50 μm this corresponds to a mean diameter of the microreservoirs in the range of preferably 0.5 to 20 μm.

The term "mean diameter" as used herein is defined as the mean value of the x, y, z-average diameters of all microreservoirs. The target particle size can be adjusted by the solids content and the viscosity of the solid dispersion.

The maximum and mean diameters of the microreservoirs as well as the number of microreservoirs per surface area of the solid dispersion can be determined as follows: The surface of the solid dispersion is examined with a light microscope (Leica microscope type DM/RBE equipped with a camera type Basler A 113C). The measurement is performed by incidental polarized light analysis using a microscope at 200× magnification. A picture analysis is performed using the software Nikon LuciaDi, Version 4.21, resulting in mean and maximum diameters for each sample.

In particular preferred embodiment, the solid dispersion represents a self adhesive matrix, such as a self adhesive matrix of a transdermal therapeutic system.

Thus, in a further aspect, the present invention relates to the use of a solid dispersion as specified above for the preparation of a transdermal therapeutic system, which comprises the solid dispersion as self adhesive matrix.

In another aspect, the present invention relates to a transdermal therapeutic system comprising a solid dispersion as specified above as self adhesive matrix.

The term "transdermal therapeutic system" (TTS) as used herein refers to a matrix-type patch having a continuous self adhesive matrix in at least its center portion, which matrix is formed by the above specified solid dispersion. Such a patch consists of a backing layer, the self adhesive matrix and a protective foil or sheet, which is removed before use.

The backing layer is inert to the components of the self adhesive matrix. It is a film being impermeable to rotigotine. Such a film may consist of polyester, polyamide, polyethylene, polypropylene, polyurethane, polyvinyl chloride or a combination of the aforementioned materials. These films may or may not be coated with an aluminum film or with aluminum vapour. The thickness of the backing layer may be between 10 and 100 μm, preferably between 15 and 40 μm.

The self adhesive matrix layer formed by the above specified solid dispersion may have a coating weight between 50 and 150 $g/m^2$, preferably between 50 and 75 $g/m^2$ and most preferably is 50 $g/m^2$±5%.

Sporadically few tiny spots or bubbles may be observed in the adhesive matrix of some patches. They are small areas where the backing film can be seen through a small hole in the adhesive matrix, and thus are referred to as "matrix-free spots". In general these spots do not occur and their occurrence does, moreover, not have any impact on the pharmaceutical quality of these patches.

In a particular preferred embodiment, the self-adhesive matrix is free of particles, which can absorb salts of rotigotine on the TTS/skin interface. Examples of particles, which can absorb salts of rotigotine on the TTS/skin interface, include silica. Such particles, which can adsorb salts of rotigotine, may represent diffusion barriers for the free base form of the drug and may result in the formation of channels inducing some permeability of the self-adhesive matrix for the protonated form of rotigotine, which is disadvantageous.

Preferably, the TTS contains less than 1 wt-% of inorganic silicates, most preferably it is completely free from inorganic silicates.

The protective foil or sheet will be removed immediately prior to use, i.e. immediately before the TTS will be brought into contact with the patient's skin. The protective foil or sheet may consist of polyester, polyethylene or polypropylene, which may or may not be coated with aluminum film or aluminum vapour or fluoropolymers. Typically, the thickness of such a protective foil or sheet ranges between 50 and 150 μm.

So as to facilitate removal of the protective foil or sheet when wishing to apply the TTS, the protective foil or sheet may comprise separate protective foils or sheets having overlapping edges, similar to the kind used with the majority of conventional plasters.

In one embodiment, the TTS has a basal surface area of 0.5 to 50 cm$^2$, and another one of about 1 to 50 cm$^2$ and in still another one of about 5 to 50 cm$^2$. In another embodiment the TTS has a basal surface area of 10 to 40 cm$^2$, and in another one of about 10 to 30 cm$^2$ and in another one of about 20 to 30 cm$^2$. It goes without saying that a device having a surface area of, say, 20 cm$^2$ is pharmacologically equivalent to and may be exchanged by two 10 cm$^2$ devices or four 5 cm$^2$ devices having the same drug content per cm$^2$. Thus, the surface areas as indicated herein should be understood to refer to the total surface of all devices simultaneously administered to a patient.

Providing and applying one or several TTS has the pharmacological advantage over oral therapy that the attending physician can titrate the optimum dose for the individual patient relatively quickly and accurately, e.g. by simply increasing the number or size of devices given to the patient. Thus, the optimum individual dosage can often be determined after a time period of only about 3 weeks with low side effects.

A preferred content of rotigotine in the TTS is in the range of 0.1 to 3.15 mg/cm$^2$. Still more preferred are 0.4 to 1.5 mg/cm$^2$ and 0.2 to 1.0 mg/cm$^2$. If a 7 day patch is desired, higher drug contents will generally be required. A rotigotine content in the range of about 0.4 to 0.5 mg/cm$^2$ has been found to be particularly advantageous in that it provides the optimum usage of the drug contained in a once-a-day TTS, i.e. there is only very little residual drug content in the TTS after administration. In a particular preferred embodiment, the rotigotine content is 0.45 mg/cm$^2$. The apparent dose administered in 24 hours by using such a TTS usually is 40 to 50% and may be intraindividually as high as 80-90% of the drug amount originally contained in the TTS. In general the content of rotigotine in the TTS can be adapted accordingly in order to provide a suitable flux for a multiple day TTS.

The TTS may be prepared by a manufacturing process, which comprises preparing a rotigotine comprising solid dispersion, i.e. the self adhesive matrix, coating, drying or cooling and laminating to get the bulk product, converting the laminate into patch units via cutting, and packaging.

After preparation, the rotigotine-comprising solid dispersion contains rotigotine to a little extent in dissolved form and mainly in amorphous form. However, for preparing the solid dispersion either of the two crystalline forms of rotigotine, i.e. polymorphic form I or polymorphic form II, may be employed as a starting material. The manufacturing process is described in more detail below.

The water content in the TTS obtained after preparation is in general low enough so that no evaporation of water during preparation of the TTS is necessary. Typically, the water content in a freshly prepared patch is below 2 wt-%, in another embodiment more preferably 1 wt-% or lower and in another embodiment 0.6 wt-% or lower, depending on the drug/PVP weight ratio.

In a particularly preferred embodiment, the TTS is a silicone-based transdermal therapeutic system comprising a mixture of at least one high tack and at least one medium tack amine-compatible silicone pressure sensitive adhesive as the main adhesive components, about 0.1 to 3.15 mg/cm$^2$ of rotigotine in the free base form as active ingredient, and polyvinylpyrrolidone, wherein the weight ratio of rotigotine to polyvinylpyrrolidone ranges from 9:3.5 to 9:6.

In a preferred embodiment rotigotine and polyvinylpyrrolidone are contained in said silicone-based transdermal therapeutic system in a multitude of microreservoirs.

In still another aspect, the present invention relates to the use of the aforementioned transdermal therapeutic systems as a medicament.

In a preferred embodiment, the medicament is used in the treatment of diseases susceptible to the action of dopamine receptor agonists, such as rotigotine.

Diseases, which may be treated include Parkinson's disease, Parkinson's plus syndrome, depression, the restless-legs syndrome and pain.

Also, the medicament may be used in the treatment or prevention of dopaminergic neurone loss.

It should be understood that the term "treatment" in the context of this application is meant to designate a treatment or an alleviation of the symptoms. The treatment may be of a therapeutic or prophylactic nature.

The invention and the best mode for carrying it out will be explained in more detail in the following non-limiting examples.

EXAMPLES

Example 1: Influence of the Rotigotine to PVP Weight Ratio on the Crystallization of Rotigotine in a TTS Sample Preparation Samples for testing the stabilizing properties of several rotigotine to polyvinylpyrrolidone weight ratios in terms of the present invention were manufactured basically following the process below.

5 g Sodium metabisulfite were dispensed in 45 g water while stirring until a clear 10% w/w/aqueous solution is obtained.

PVP Solution

Polyvinyl pyrrolidone (Kollidon 90 F) (5 g) was added to 14.8 g anhydrous ethanol while stirring and leave the solution for swelling. After swelling the mixture is stirred until the polyvinyl pyrrolidone is entirely dissolved. After the complete dissolution of the polyvinyl pyrrolidone, an aqueous 10% w/w sodium metabisulfite solution (0.022 g), 0.05 g ascorbyl palmitate and 0.124 g all-rac-α-tocopherol are added. The mixture is stirred until a clear ethanolic PVP solution is obtained.

PVP-Rotigotine-Solution

An ethanolic PVP solution as described above (15.998 g) are dissolved in anhydrous ethanol (42.33 g) and the mixture is heated to 30-40° C. while stirring. Then (−)-5,6,7,8-tetrahydro-6-[propyl-[2-(2-thienyl)ethyl]-amino]1-naphthalenol (rotigotine, 18 g, polymorphic form I) was added to this solution. The mixture is stirred and heated to 50-60° C.

105.75 g of an amine resistant high tack silicone adhesive (BIO-PSA® Q7-4301 mfd. by Dow Corning) (70 wt-% solution in heptane), 105.72 g of an amine resistant medium tack silicone adhesive (BIO-PSA® Q7-4201 mfd. by Dow Corning) (70 wt-% solution in heptane), 63.54 g of the PVP-rotigotine-solution obtained above were mixed and all components were stirred until a homogenous dispersion was obtained.

The dispersion was coated onto a suitable fluoropolymer coated polyester release liner (e.g. SCOTCHPAK® 9744) with a suitable doctor knife and the solvents were continuously removed in a drying oven at temperatures up to 80° C. for about 30 min to obtain a drug-containing adhesive matrix of 50 g/m² coating weight. The dried matrix film was laminated with a polyester-type backing foil (e.g. Hostaphan MN 19). The individual patches were punched out of the complete laminate in the desired sizes (e.g. 10 cm², 20 cm², 30 cm²) and sealed into pouches under the flow of nitrogen.

Table 1 shows the composition in mg/20 cm² of the thus obtained rotigotine patch, which comprises rotigotine and polyvinylpyrrolidone in a weight ratio of 9:2 (comparative example)

TABLE 1

Composition in mg/20 cm² of rotigotine patch 9:2

| Component | Amount (mg) |
|---|---|
| Rotigotine Base | 9.00 |
| Polyvinylpyrrolidone | 2.00 |
| Silicone BIO-PSA ® Q7-4301 | 44.47 |
| Silicone BIO-PSA ® Q7-4201 | 44.46 |
| Ascorbyl palmitate | 0.02 |
| DL-alpha Tocopherol | 0.05 |
| Sodium metabisulfite | 0.0006 |
| Matrix coating weight | 50 g/m² |

The above manufacturing process was adapted to the varying amounts of polyvinylpyrrolidone and the slightly increased coating weight of sample Nos. 1-8 (cf. Table 2 below).

The rotigotine to polyvinylpyrrolidone weight ratio of 9:2 of sample No. 1 corresponds to the rotigotine to polyvinylpyrrolidone weight ratio of Neupro®.

During manufacturing of sample No. 2 and sample No. 3 disintegration tendencies of the suspension were observed during the coating process. That is, compositions based on rotigotine to polyvinylpyrrolidone weight ratios of 9:1 and 9:1.6 were not processable.

The 9:11 formulation of sample No. 8 was only processable under heating during mixing the rotigotine/PVP solution with the adhesives and coating due to the high viscosity resulting from the high amount of PVP.

Based on the rotigotine to polyvinylpyrrolidone weight ratio of 9:4 of sample 5, the above manufacturing process was further adapted to a reduced content of rotigotine and polyvinylpyrrolidone as well as an amended ratio of the used silicone adhesives and an increased matrix coating weight (sample 9):

5.000 kg polyvinylpyrrolidone (Kollidon F 90) were dissolved in 33.81 kg anhydrous ethanol and the obtained solution was mixed with 0.0238 kg of an aqueous sodium bisulfate solution (10% w/w), 0.0367 kg ascorbyl palmitate and 0.09291 kg DL-α-tocopherol.

18.033 kg of the thus obtained solution were heated to 30-40° C. while stirring and 5.199 kg crystalline rotigotine free base (polymorphic form II) were added to this solution in several portions. The mixture was stirred and further heated up to 50-60° C. for approximately 1-2 hours to completely dissolve the drug.

18.764 kg of the ethanolic drug/polyvinylpyrrolidone solution were added to a mixture of 60.83 kg BIO-PSA Q7 4301 (70 wt-% solution in heptane) and 30.41 kg BIO-PSA Q7 4201 (70 wt-% solution in heptane) and it was stirred for at least 1 hour until a homogenous dispersion was obtained.

The dispersion was coated onto a fluoropolymer coated release liner and the solvents were continuously removed in a drying oven at temperatures ranging from 40° C. up to 115° C. to obtain a dry drug-containing adhesive matrix of 75 g/m² coating weight. The dried matrix film was laminated with a polyester-type backing foil being siliconized on the inner side and aluminium vapor coated on the opposite side. The individual patches were punched out of the complete laminate and were sealed into pouches under nitrogen flow.

TABLE 2

Rotigotine to polyvinylpyrrolidone weight ratios and coating weights of sample Nos. 1-9

| | Sample No. | | | | | | | | |
|---|---|---|---|---|---|---|---|---|---|
| | 1 | 2 | 3 | 4 | 5 | 6 | 6 | 8 | 9 |
| Rotigotine:PVP [weight ratio] | 9:2 | 9:1 | 9:1.6 | 9:3 | 9:4 | 9:6 | 9:8 | 9:11 | 9:4 |
| Coating weight [g/m²] | 60 | 62 | 62 | 61 | 59 | 63 | 61 | 63 | 75 |

Analytical Methods

Drug release was determined using Apparatus 5 (Paddle Over Disk) as described in the United States Pharmacopeia (USP 31-NF 26), Chapter 724 "Drug Release". United States Pharmacopeia Convention, Inc.: Rockville, Md., 2008 using the following conditions: dissolution medium: 900 ml phosphate buffer pH 4.5; temperature adjusted to 32±0.5° C.; paddle rotation speed: 50 rpm; sampling times: 0.25, 0.5, 1, 2 and 3 h, respectively.

The released drug amounts were determined by a validated RP HPLC-method at a detection wave length of 272 nm.

Stability testing was performed with one patch of each sample. The tests were performed from 0 weeks up to 8 weeks for samples 1 to 9 and up to 24 months for further patch samples of a rotigotine:PVP weight ratio of 9:2, 9:3 and 9:4 after the production date under open storage conditions of 25° C./60% RH and the occurrence of crystals was recorded by taking microscopic pictures. These results were confirmed by DSC for selected samples.

Analytical Results

Results from drug release testing of samples 1-8 are shown in FIG. 1.

Only sample Nos. 1, 5 and 6 meet the specifications set for drug release of the marketed Neupro® patch having a comparable matrix thickness. In vitro drug release of sample 9 (not shown) having a reduced content of rotigotine and polyvinylpyrrolidone and an increased matrix thickness also meets the Neupro® specification after 3 hours, i.e. the endpoint of the test. For all remaining samples, the amount of rotigotine, which is released from the respective TTS during release testing is less than the specified lower limit.

Results from microscopic inspection of sample Nos. 1-9 are shown in Table 3.

For the rotigotine to polyvinylpyrrolidone weight ratios of 9:1 and 9:1.6 undissolved rotigotine crystals could microscopically be determined already in the freshly manufactured product. This finding could be confirmed by DSC measurements and reflects the problems occurring during manufacturing described above for these samples.

Starting with the first week crystals were observed for the rotigotine to polyvinylpyrrolidone weight ratios of 9:2 and 9:3.

Figure 2:
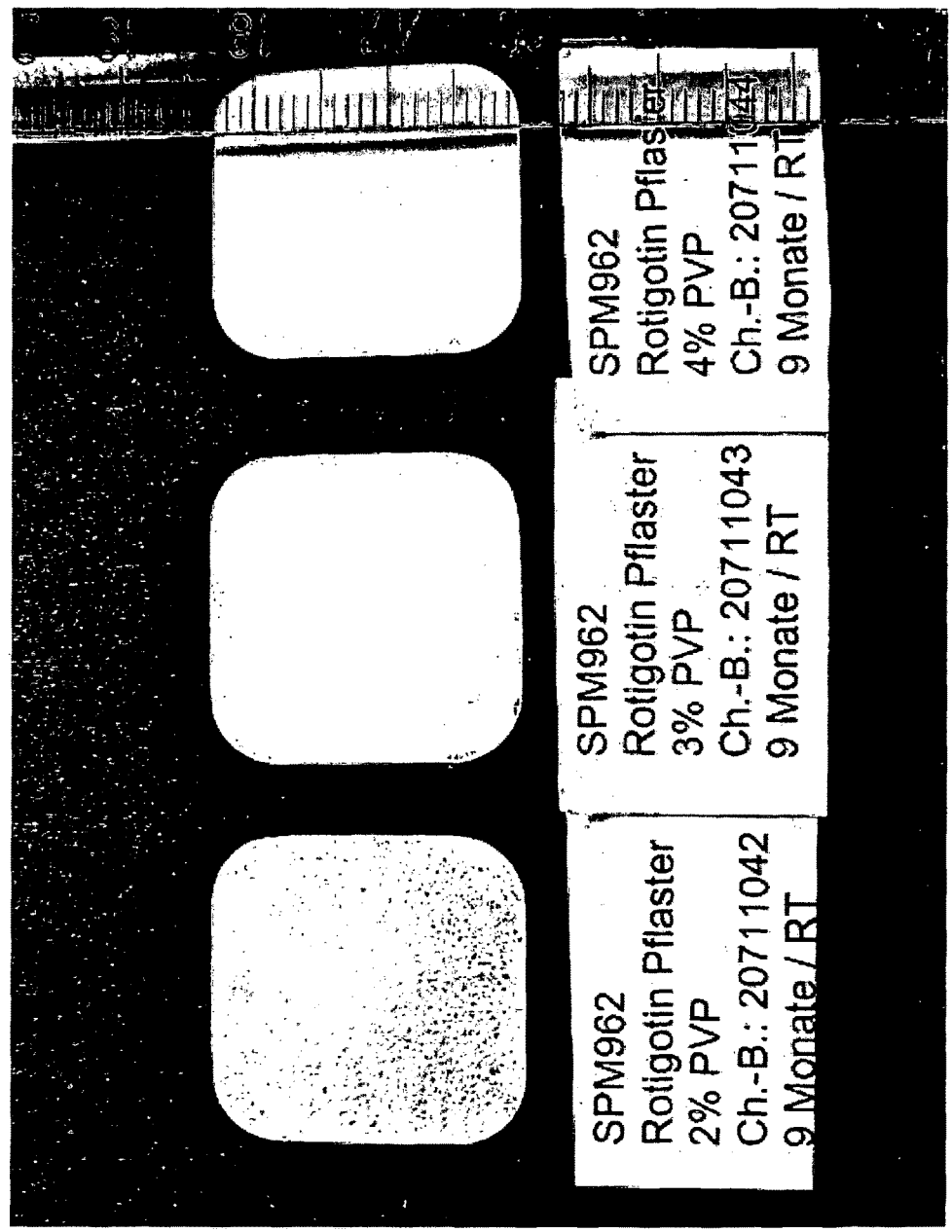
FIG. 2 shows the physical stability of rotigotine patches containing different amounts of PVP (rotigotine:PVP weight ratio of 9:2, 9:3 and 9:4) after 9 month at room temperature.
Figure 3:
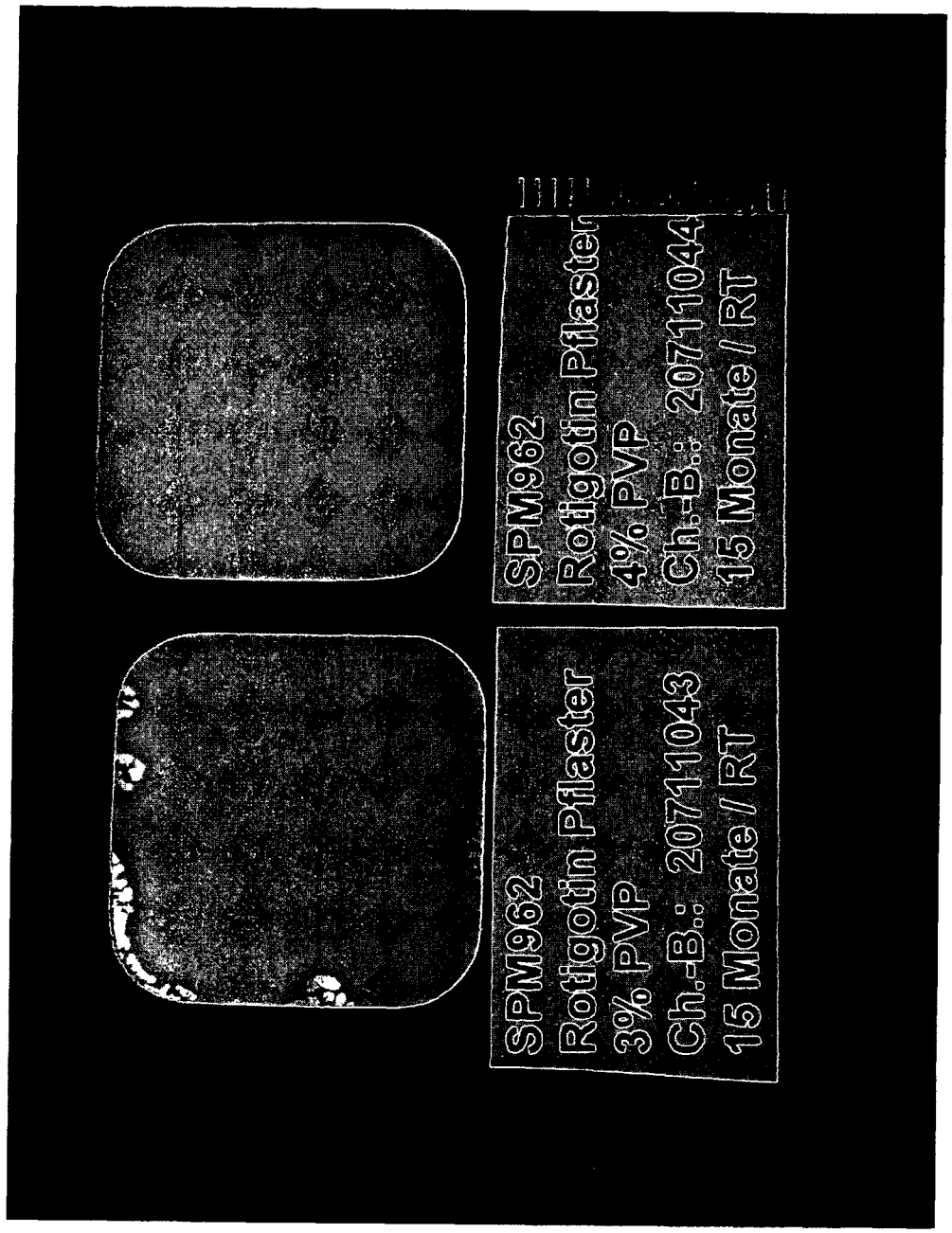
FIG. 3 shows the physical stability of rotigotine patches containing different amounts of PVP (rotigotine:PVP weight ratio of 9:3 and 9:4) after 15 month at room temperature.
Figure 4:
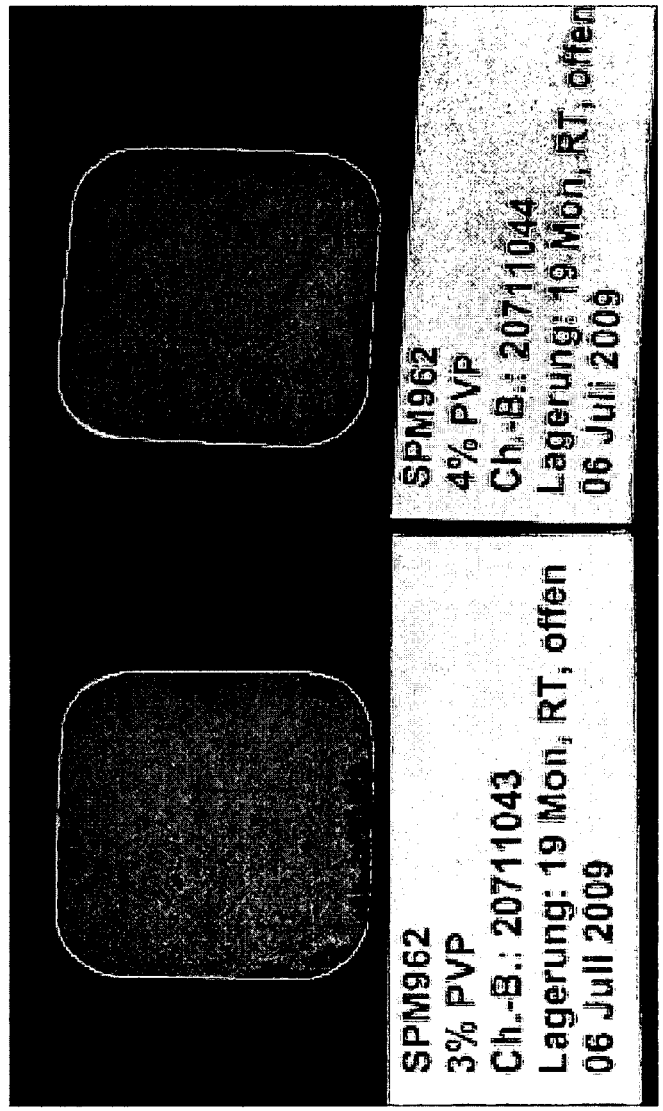
FIG. 4 shows the physical stability of rotigotine patches containing different amounts of PVP (rotigotine:PVP weight ratio of 9:3 and 9:4) after 19 month at room temperature.

FIGS. 2 to 4 show that during long term stability testing of patches comprising different ratios of rotigotine to polyvinylpyrrolidone at room temperature an increasing amount of crystals was observed for the rotigotine to polyvinylpyrrolidone weight ratios of 9:2 and 9:3, whereas no crystal formation was observed for the rotigotine to polyvinylpyrrolidone weight ratio of 9:4 (sample 5).

During long term testing of patches with a rotigotine to polyvinylpyrrolidone weight ratio of 9:4 (sample 5) for up to 24 months at room temperature no crystals were observed.

Also sample 9 with a rotigotine to polyvinylpyrrolidone weight ratio of 9:4 and having a reduced content of rotigotine and polyvinylpyrrolidone and an increased matrix thickness did not show any crystallization phenomena after long-term storage for up 18 months at 25° C.

An increasing PVP content delayed crystal appearance as it is shown for the rotigotine to polyvinylpyrrolidone weight ratios of 9:4 up to 9:11.

TABLE 3

Results from storage stability testing of sample Nos. 1-9 at 25° C./60% RH (+ = crystals, - = no crystals)

| | Sample No. | | | | | | | | |
|---|---|---|---|---|---|---|---|---|---|
| | 1 | 2 | 3 | 4 | 5 | 6 | 7 | 8 | 9 |
| Rotigotine:PVP [weight ratio] | 9:1 | 9:1.6 | 9:2 | 9:3 | 9:4 | 9:6 | 9:8 | 9:11 | 9:4 |
| 0 weeks | + | + | - | - | - | - | - | - | - |
| 1 week | + | + | + | + | - | - | - | - | - |
| 4 weeks | + | + | + | + | - | - | - | - | - |
| 8 weeks | + | + | + | + | - | - | - | - | - |

That is, taking also the above discussed data from release testing into account, optimum results could be achieved with rotigotine to polyvinylpyrrolidone weight ratios between 9:4 and 9:6. Higher ratios failed to sufficiently prevent rotigotine from crystallization and made the system prone to crystal growth or were even unprocessable. Lower ratios led to insufficient drug release by reducing the amount of rotigotine, which is released from the patch, below those values specified for the marketed Neupro® patch.

The invention claimed is:

1. A method for stabilizing rotigotine, the method comprising providing a solid dispersion comprising polyvinylpyrrolidone and a non-crystalline form of rotigotine free base, wherein the weight ratio of rotigotine free base to polyvinylpyrrolidone is in a range from about 9:4 to about 9:6.

2. A solid dispersion comprising a dispersing agent and a dispersed phase, said dispersed phase comprising rotigotine free base and polyvinylpyrrolidone, wherein the weight ratio of rotigotine free base to polyvinylpyrrolidone is in a range from about 9:4 to about 9:6.

3. The solid dispersion of claim 2, wherein the solubility of rotigotine free base in the dispersing agent is below 1 wt-%.

4. The solid dispersion of claim 2, wherein the dispersing agent comprises at least one silicone pressure sensitive adhesive.

5. The solid dispersion of claim 2, wherein the dispersing agent comprises a mixture of a first silicone pressure sensitive adhesive and a second silicone pressure sensitive adhesive and wherein the solid dispersion has a complex viscosity between 5 and 15 MP.

6. The solid dispersion of claim 2, wherein rotigotine free base and polyvinylpyrrolidone are in a multitude of microreservoirs.

7. A pharmaceutical composition comprising a solid dispersion according to claim 2.

8. A transdermal therapeutic system comprising at least one amine-compatible silicone pressure sensitive adhesive, about 0.1 to about 3.15 mg/cm' of rotigotine free base, and polyvinylpyrrolidone, wherein the weight ratio of rotigotine free base to polyvinylpyrrolidone is in a range from about 9:4 to about 9:6.

9. The transdermal therapeutic system of claim 8, wherein rotigotine free base and polyvinylpyrrolidone are contained in a multitude of microreservoirs.

10. A transdermal therapeutic system comprising a solid dispersion of claim 2.

11. A method for preparing a transdermal therapeutic system, the method comprising preparing a solid dispersion comprising a dispersing agent and a dispersed phase, said dispersed phase comprising rotigotine free base and polyvinylpyrrolidone, wherein the weight ratio of rotigotine free base to polyvinylpyrrolidone is in a range from about 9:4 to about 9:6.

12. The method of claim 1, wherein the solid dispersion further comprises a dispersing agent.

13. The method of claim 12, wherein the dispersing agent comprises at least a first adhesive having a complex viscosity between 40 and 250 MP.

14. The method of claim 13, wherein the dispersing agent comprises at least a second adhesive having a complex viscosity between 1 and 10 MP.

15. The method of claim 14, wherein the dispersing agent has a complex viscosity between 5 and 25 MP.

16. The method of claim 12, wherein the dispersing agent comprises at least a first adhesive and a second adhesive and the solid dispersion has a complex viscosity between 5 and 15 MP.

17. The method of claim 12, wherein the dispersing agent comprises at least a first adhesive and a second adhesive and the solid dispersion has a peel adhesion between 3 and 16 N/50 mm at a thickness of 50 g/m$^2$ and/or a peel adhesion between 14 and 26 N/50 mm at a thickness of 150 g/m$^2$.

18. The method of claim 12, wherein the dispersing agent comprises at least a first adhesive and a second adhesive and the solid dispersion has a static shear adhesion between 20 and 150 min.

19. The solid dispersion of claim 2, wherein the dispersing agent comprises at least a first adhesive having a complex viscosity between 40 and 250 MP.

20. The solid dispersion of claim 2, wherein the dispersing agent comprises at least a second adhesive having a complex viscosity between 1 and 10 MP.

21. The solid dispersion of claim 20, wherein the dispersing agent has a complex viscosity between 5 and 25 MP.

22. The solid dispersion of claim 2, wherein the dispersing agent comprises at least a first adhesive and a second adhesive and the solid dispersion has a complex viscosity between 5 and 15 MP.

23. The solid dispersion of claim 2, wherein the dispersing agent comprises at least a first adhesive and a second adhesive and the solid dispersion has a peel adhesion between 3 and 16 N/50 mm at a thickness of 50 g/m$^2$ and/or a peel adhesion between 14 and 26 N/50 mm at a thickness of 150 g/m$^2$.

24. The solid dispersion of claim 2, wherein the dispersing agent comprises at least a first adhesive and a second adhesive and the solid dispersion has a static shear adhesion between 20 and 150 min.

* * * * *

UNITED STATES PATENT AND TRADEMARK OFFICE
CERTIFICATE OF CORRECTION

PATENT NO.        : 10,130,589 B2
APPLICATION NO.   : 15/884587
DATED             : November 20, 2018
INVENTOR(S)       : Hans-Michael Wolff et al.

Page 1 of 1

It is certified that error appears in the above-identified patent and that said Letters Patent is hereby corrected as shown below:

In the Specification

At Column 4, Line number 25, after "9:6", insert --.--;

At Column 5, Line number 11, replace "Aktiengesellehaft" with --Aktiengesellchaft--;

At Column 7, Line number 5, replace "1.4" with --14--;

At Column 7, Line number 31, replace "m 5 kg," with --m=5 kg,--;

At Column 8, Line number 5, replace "inverted" with --Inverted--;

At Column 8, Line number 15, replace "55145" with --55/45--;

At Column 8, Line number 33, replace "according," with --according--;

At Column 9, Line number 18, replace "w-%)." with --wt-%).--;

In the Claims

Claim number 8, Line number 16, replace "mg/cm'" with --mg/cm2--.

Signed and Sealed this
Twenty-sixth Day of November, 2019

Andrei Iancu
*Director of the United States Patent and Trademark Office*